US006271206B1

(12) United States Patent
Pillai et al.

(10) Patent No.: US 6,271,206 B1
(45) Date of Patent: Aug. 7, 2001

(54) SONIC NEBULIZED NUCLEIC ACID/CATIONIC LIPOSOME COMPLEXES AND METHODS FOR PULMONARY GENE DELIVERY

(75) Inventors: Raviraj S. Pillai, Landsdale, PA (US); Alain Rolland, The Woodlands, TX (US)

(73) Assignee: Valentis, Inc., The Woodlands, TX (US)

( * ) Notice: Subject to any disclaimer, the term of this patent is extended or adjusted under 35 U.S.C. 154(b) by 0 days.

(21) Appl. No.: 08/929,299

(22) Filed: Sep. 11, 1997

Related U.S. Application Data

(60) Provisional application No. 60/026,183, filed on Sep. 12, 1996.

(51) Int. Cl.[7] .......................... A61K 48/00; C12N 15/88; C12N 15/63

(52) U.S. Cl. .......................... 514/44; 435/320.1; 435/455; 435/458; 424/450

(58) Field of Search ..................................... 435/455, 458, 435/320.1; 514/44; 536/23.1, 23.5; 424/450

(56) References Cited

U.S. PATENT DOCUMENTS

| | | | | |
|---|---|---|---|---|
| 3,690,317 | * | 9/1972 | Millman | 128/194 |
| 5,616,334 | * | 4/1997 | Janoff et al. | 424/404 |
| 5,636,160 | * | 6/1997 | Stutts, III et al. | 424/45 |
| 5,641,662 | * | 6/1997 | Debs | 435/455 |
| 5,756,353 | * | 5/1998 | Debs | 435/375 |

FOREIGN PATENT DOCUMENTS

| | | |
|---|---|---|
| WO 92/07091 | 4/1992 | (WO) . |
| WO 92/11025 | 7/1992 | (WO) . |
| WO 93/09130 | 5/1993 | (WO) . |
| WO 93/12240 | 6/1993 | (WO) . |
| WO 93/12756 | 7/1993 | (WO) . |

OTHER PUBLICATIONS

Boucher (TIG, vol. 12, 3: 83–84, 1996).*

Anderson, Nature, vol. 392, 25–30, Apr. 19, 1998.*

Curiel et al. (Am. J. Respir. Cell Mol. Biol. vol. 14, pp. 1–18, 1996).*

Farhood et al., "Cationic Liposomes for Direct Gene Transfer in Therapy of Cancer and Other Diseases," *Annals of the New York Academy of Sciences 716*: 23–35, 1994.

Gao and Huang, "A Novel Cationic Liposome Reagent for Efficient Transfection of Mammalian Cells," *Biochemical and Biophysical Research Communications 179*(1): 280–285, 1991.

Pillai et al., "Generation of Concentrated Aerosols for Inhalation Studies," *J. Aerosol Sci. 25*(1): 187–197, 1994.

Renz et al., "Specific Vβ T Cell Subsets Mediate the Immediate Hypersensitivity Response to Ragweed Allergen," *The Journal of Immunology 151*(4): 1907–1917, 1993.

Schwarz et al., "Delivery of DNA–Cationic Liposome Complexes by Small–Particle Aerosol," *Human Gene Therapy 7*: 731–741, 1996.

Tomlinson and Rolland, "Controllable gene therapy Pharmaceutics of non–viral gene delivery systems," *Journal of Controlled Release 39*: 357–372, 1996.

Wasan et al., "Plasmid DNA Is Protected against Ultrasonic Cavitation–Induced Damage When Complexed to Cationic Liposomes," *Journal of Pharmaceutical Sciences 85*(4): 427–433, 1995.

* cited by examiner

*Primary Examiner*—Dave Trong Nguyen
(74) *Attorney, Agent, or Firm*—Seed Intellectual Property Law Group PLLC

(57) ABSTRACT

Compositions and methods are provided for gene delivery to the respiratory tract. In particular, compositions comprising a nebulized nucleic acid/stabilizing agent complex, and methods employing such complexes for pulmonary gene delivery, are provided. Such complexes are preferably sonic nebulized.

22 Claims, 9 Drawing Sheets

SONIC NEBULIZED NUCLEIC ACID/ CATIONIC LIPOSOME COMPLEXES AND METHODS FOR PULMONARY GENE DELIVERY

CROSS-REFERENCE TO RELATED APPLICATION

The present application claims priority from U.S. Provisional Application No. 60/026,183, filed Sep. 12, 1996, which application is incorporated herein by reference in its entirety.

TECHNICAL FIELD

The present invention relates generally to the field of gene delivery to respiratory epithelial cells. The invention is more particularly related to compositions comprising a nebulized nucleic acid/stabilizing agent complex, and to methods employing such complexes for nucleic acid delivery to a patient.

BACKGROUND OF THE INVENTION

Gene delivery via inhalation is a technique that shows considerable promise for the treatment and prevention of a variety of diseases, but its application has been limited by practical difficulties. In particular, safety concerns have slowed the development of some methods of aerosol gene delivery, particularly those involving viral-based systems, and the application of other delivery methods has been limited by efficiency problems. One promising approach for gene delivery involves the use of lipid-based carriers, or liposomes. However, as with other carriers, liposomes have been inefficient for nucleic acid delivery using the drug delivery devices commonly employed.

Pharmaceutical devices that have been employed for aerosol drug delivery include metered dose inhalers (MDIs), dry powder inhalers (DPIs) and air-jet nebulizers. While such devices are suitable for the delivery of some therapeutic agents, gene delivery via these devices presents practical problems. MDIs have not been used for gene delivery because of the difficulty of formulating plasmids with propellant mixtures. DPIs are also not suitable for gene delivery because a prohibitively high inspiratory air flow rate is required to achieve effective dispersion of powder blends.

Currently, the most practical pharmaceutical device for gene delivery is the air-jet nebulizer. This device uses a compressed air source to deliver a high velocity air-jet through an orifice to create a venturi effect that draws liquid from a reservoir into an air flow stream. The differential velocity between the air and the liquid causes the liquid to break up into droplets, the majority of which are in the respirable range (1–5 μm). The jet nebulizer has been preferred for lipid-based gene delivery because of the comparative ease of formulation (e.g., often the parenteral formulation can be used directly), versatility in dose adjustment (concentration and frequency), affordability and time-proven delivery technology. The drug reservoir of the nebulizer can also be designed to administer high doses of aerosolized therapeutic agents to the lungs.

Significant drawbacks remain, however, with gene delivery using a jet nebulizer, including lack of portability, output variability between units, large dead volumes and variation in solution versus solvent output. The delivery efficiency (defined as the ratio of mass of drug nebulized to mass of drug deposited in the lower airways) is very low—less than 2%. This low delivery efficiency may be attributable to constant air flow through the system, resulting in continuous atomization and concomitant dilution of the output aerosol stream. Further, using a jet nebulizer, aerosols are generated even during exhalation, which accounts for 60% of the respiratory cycle.

Accordingly, there is a need in the art for improved methods of pulmonary gene delivery. The present invention fulfills these needs and further provides other related advantages.

SUMMARY OF THE INVENTION

Briefly stated, the present invention provides compositions and methods for pulmonary gene delivery. In one aspect, the present invention provides a nucleic acid delivery apparatus. The apparatus comprises, in one embodiment, (a) a sonic nebulizer, (b) a nucleic acid and (c) a stabilizing agent, wherein the nucleic acid and stabilizing agent are contained within the sonic nebulizer. In a related embodiment, the nucleic acid(s) and stabilizing agent(s) are provided in a separate container, the sonic nebulizer being adapted to receive the container and produce an aerosol suitable for inhalation therefrom.

In another aspect, methods are provided for preparing a sonic nebulized nucleic acid/stabilizing agent complex, comprising the steps of: (a) combining at least one nucleic acid with at least one stabilizing agent to form a complex and (b) forming an aerosol of the complex with a sonic nebulizer.

In a related aspect, the present invention provides a sonic nebulized nucleic acid/stabilizing agent complex, wherein the complex comprises at least one nucleic acid and at least one stabilizing agent, and wherein the complex is sonic nebulized to form an aerosol.

In a further aspect, the present invention provides methods for treating a patient with a sonic nebulized nucleic acid/stabilizing agent complex, comprising the step of providing a sonic nebulized nucleic acid/stabilizing agent complex to a patient, wherein the complex is suitable for inhalation by said patient. In a related aspect, a method for treating a patient with a nucleic acid encoding a therapeutic protein is disclosed, comprising the step of providing a complex as discussed above to a patient, wherein the complex is suitable for inhalation by the patient.

In yet another related aspect, methods are provided for treating a patient with a sonic nebulized nucleic acid/stabilizing agent complex, comprising the steps of: (a) combining at least one nucleic acid with at least one stabilizing agent to form a complex; (b) forming an aerosol of the complex with a sonic nebulizer, and (c) providing the aerosol for inhalation by a patient.

In still further aspects, the present invention provides methods for treating a patient with a nebulized nucleic acid/stabilizing agent complex, comprising the step of providing a nebulized nucleic acid/stabilizing agent complex to a patient, wherein the stabilizing agent comprises a cationic lipid, has a net positive charge, and is suitable for inhalation by the patient.

In a related aspect, methods are provided for treating a patient with a nebulized nucleic acid/cationic lipid complex, comprising the steps of: (a) combining at least one nucleic acid with at least one cationic lipid to form a complex having a net positive charge; (b) forming an aerosol of the complex with a nebulizer; and (c) providing the aerosol for inhalation by a patient.

These and other aspects of the present invention will become apparent upon reference to the following detailed description and attached drawings. All references disclosed herein are hereby incorporated by reference in their entirety as if each was incorporated individually.

Deposited dose=aerosol concentration (μg/L)×volume of air breathed (L)×deposition fraction.

The aerosol concentration was determined by sampling the aerosols on a filter at a pre-determined flow rate using a critical flow orifice. The volume of air breathed was estimated from the ventilatory parameters of the animals (Harkness and Wagner, "The Biology and Medicine of Rabbits and Rodents," Lea and Febiger, Philadelphia, 1983). Deposition models were used to estimate the fraction of aerosol deposited in the lower airways (Schlesinger, "Deposition and Clearance of Inhaled Particles," In R. O. McClellan and R. T. Henderson eds., "Concepts in Inhalation Toxicology," Hemisphere Publishing Corporation, New York, 1988).

Figure 6:
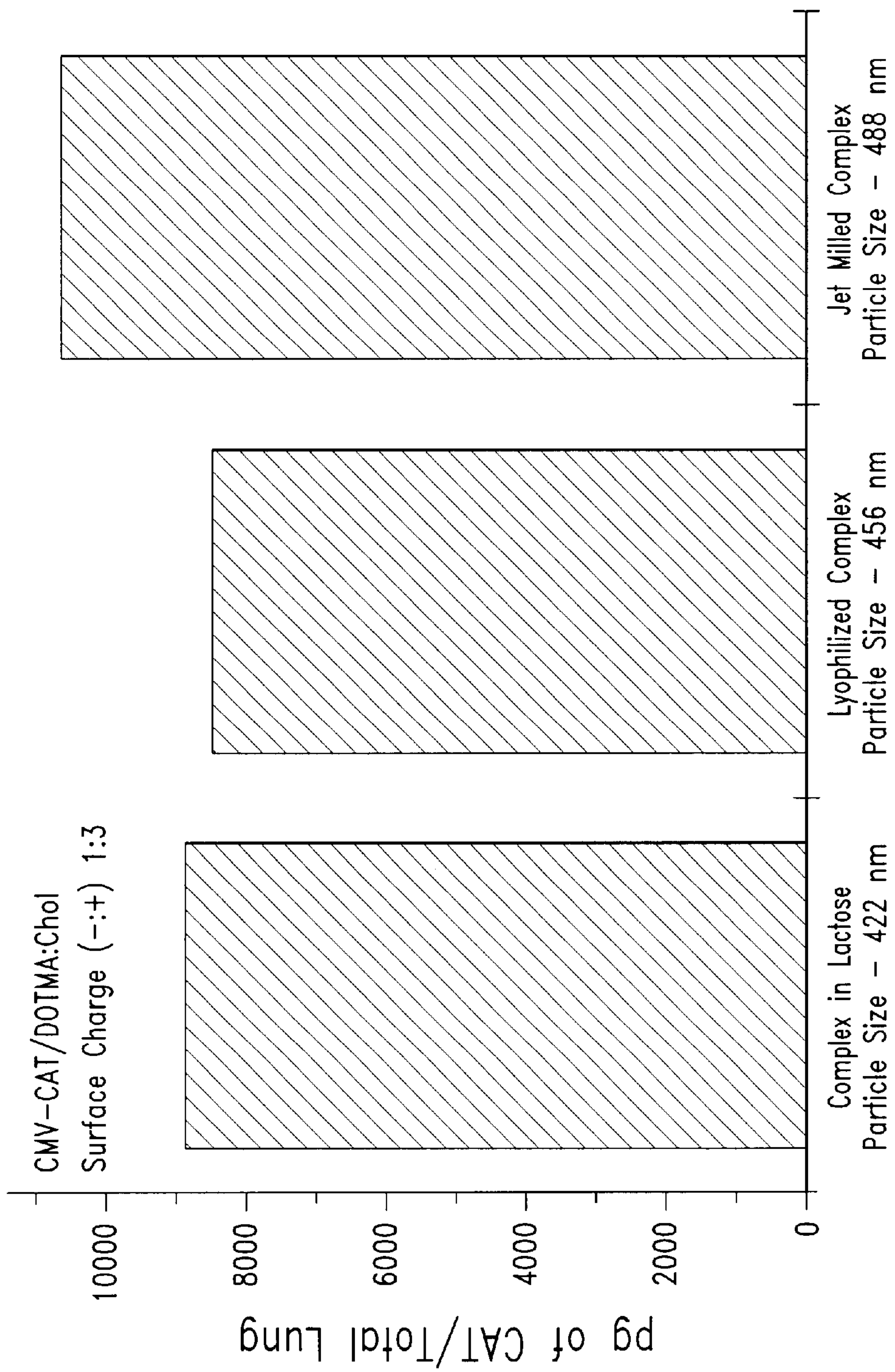

FIG. 6 is a graph depicting the level of CAT expression (pg CAT per total lung) in rat lungs following intratracheal instillation of representative lyophilized and jet milled nucleic acid/stabilizing agent complexes upon rehydration to isotonicity with water. CMV-CAT/DOTMA:Chol complexes (with a 1:3 (−:+) charge ratio) were instilled with a DNA dose of 50 μg. Column 1 shows the level of expression in the positive control rats (instilled with CMV-CAT/DOTMA:Chol formulated in 10% lactose, particle size 422 nm); column 2 illustrates the level of CAT expression following instillation with the lyophilized complex (456 nm particle size) and column 3 shows the level of expression following instillation with the jet milled complex (488 nm particle size).

Figure 7:
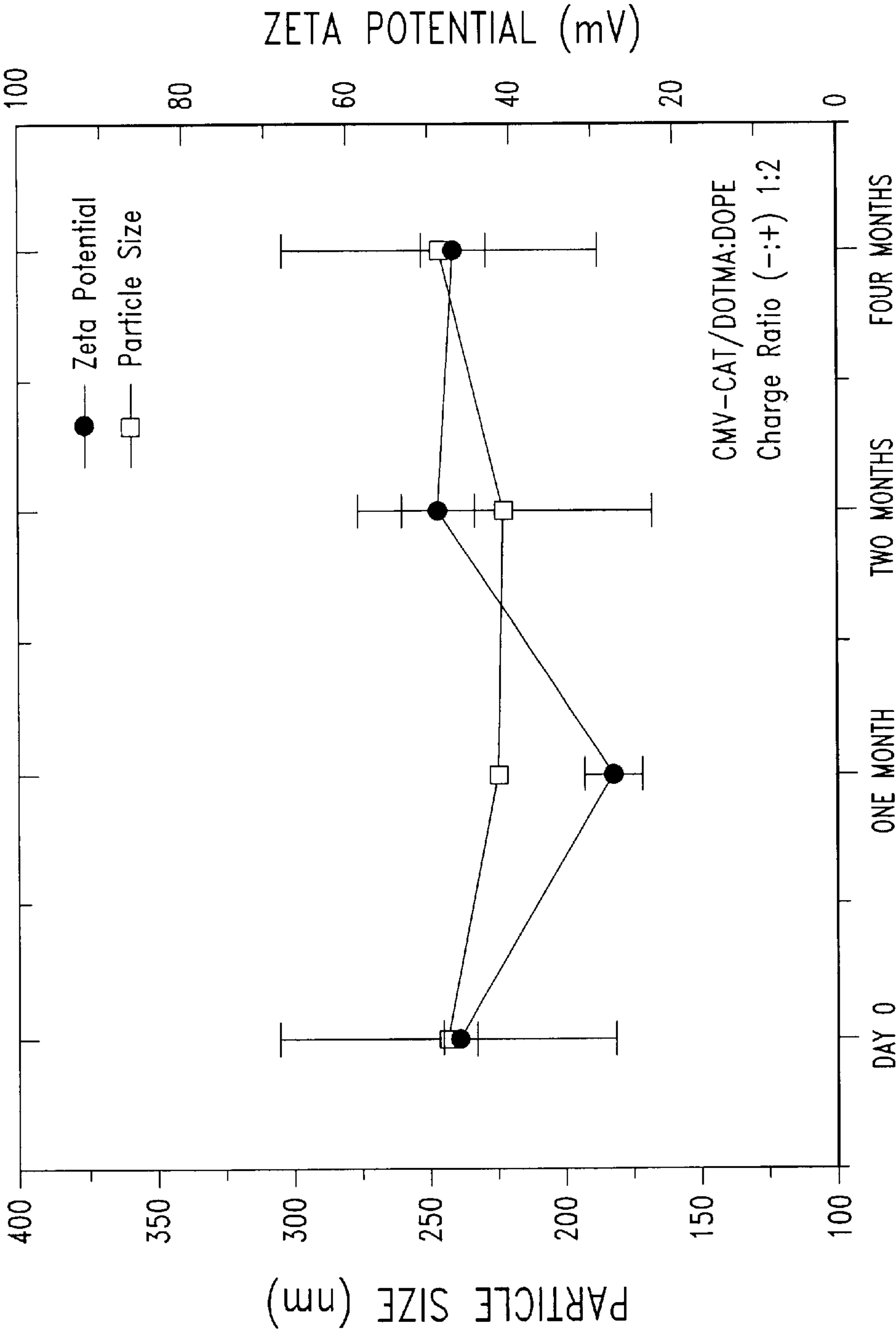

FIG. 7 is a graph illustrating the stability of lyophilized plasmid/lipid complex. CMV-CAT/DOTMA:Chol complexes (with a 1:2 (−:+) charge ratio) were lyophilized and reconstituted to isotonicity. Particle size (in nm) and zeta potential (in mV) measured on Day 0 and at one, two and four months later are shown.

Figure 8:
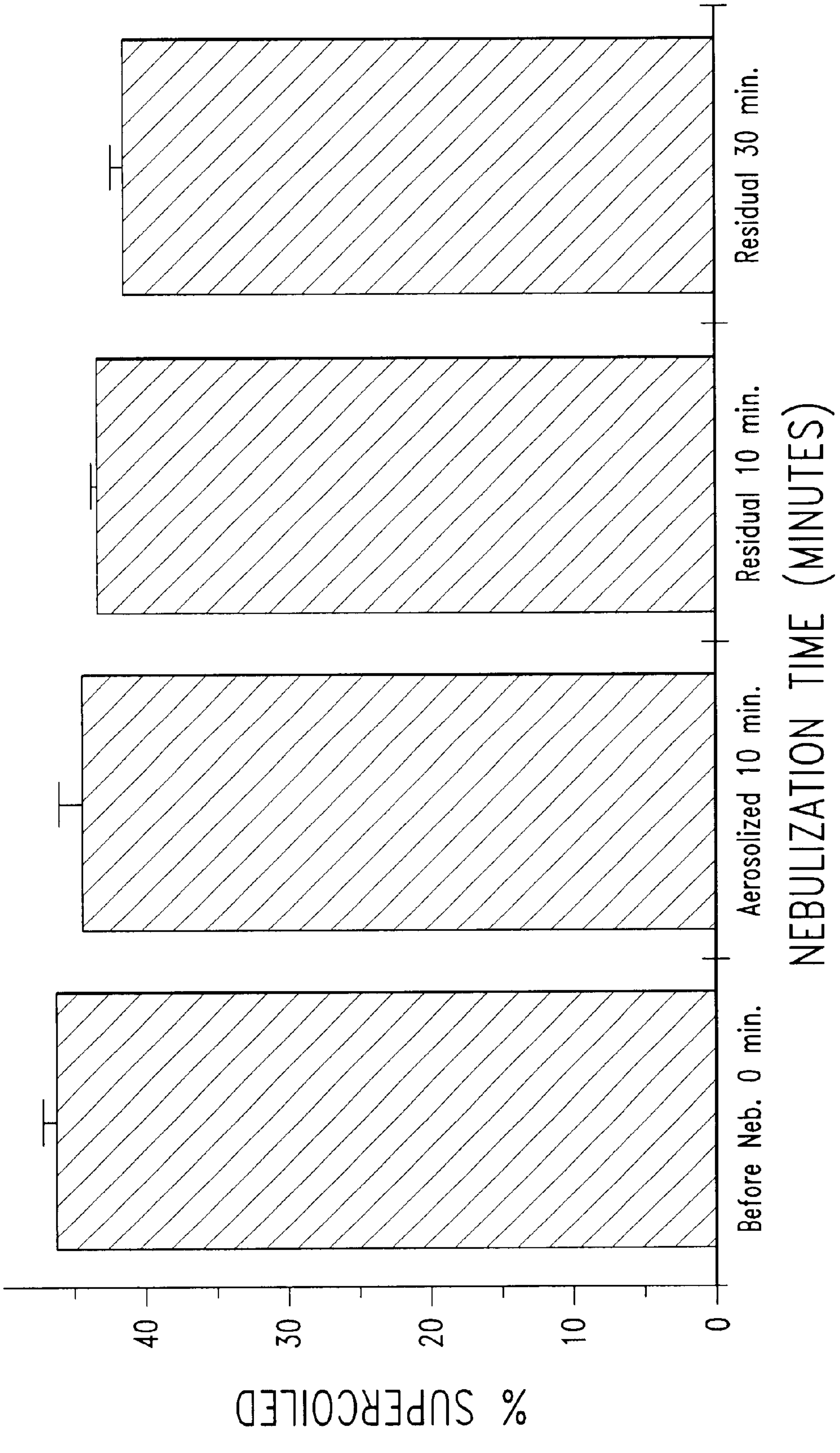

FIG. 8 is a graph depicting the fraction of supercoiled form of a representative plasmid in unnebulized, aerosolized and residual plasmid/lipid complexes. Column 1 shows the percent supercoiled for the unnebulized complex, column 2 shows the percent supercoiled for the complex aerosolized for 10 minutes and columns 3 and 4 show the percent supercoiled for the residual complex after 10 and 30 minutes, respectively.

Figure 9:
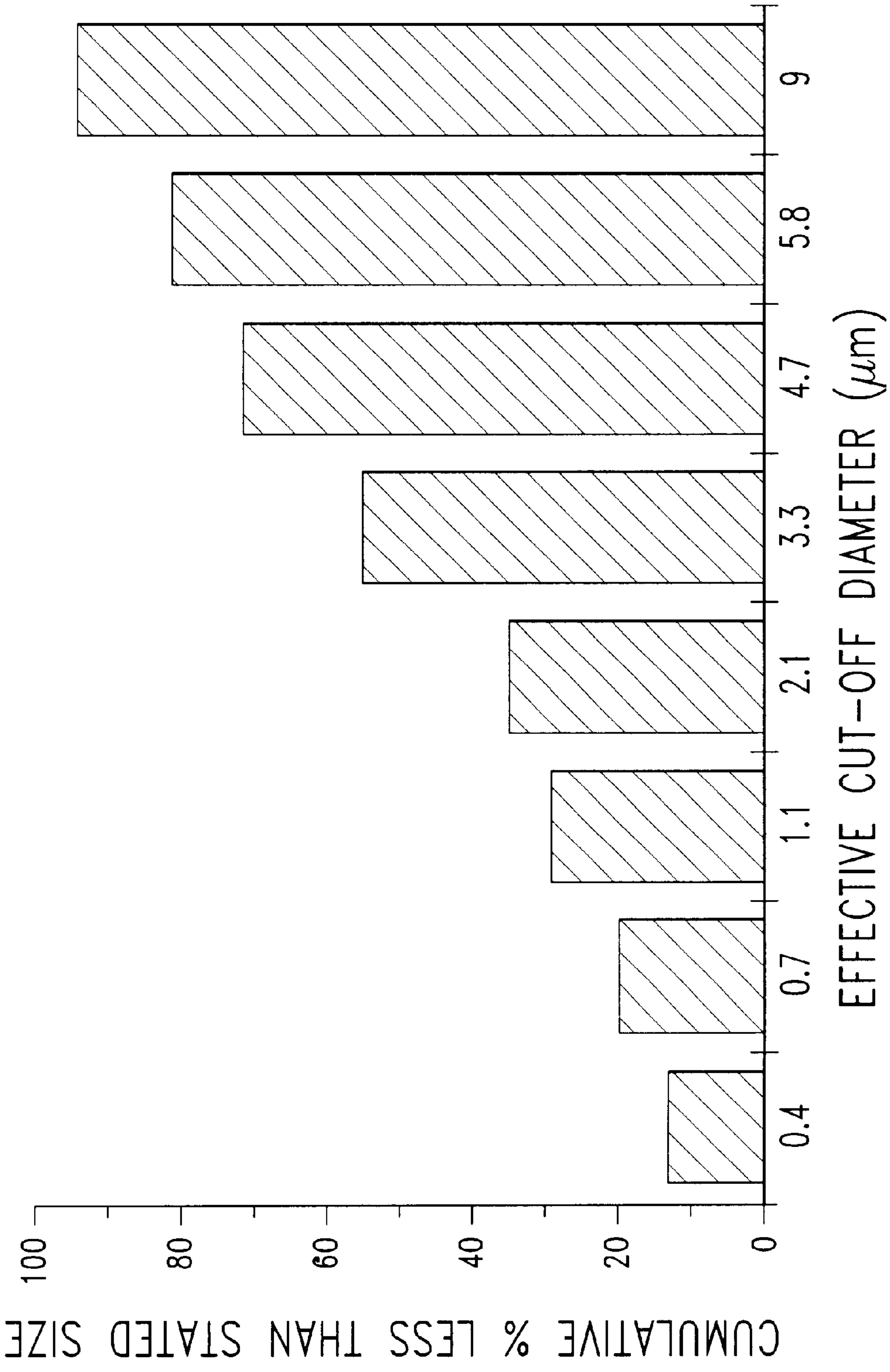

FIG. 9 is a graph showing the size distribution (presented as the cumulative percent less than a series of effective cut-off diameters) of an aerosolized plasmid/lipid complex from an ultrasonic nebulizer. The effective cut-off diameters shown are 0.4 μm (column 1), 0.7 μm (column 2), 1.1 μm (column 3), 2.1 μm (column 4), 3.3 μm (column 5), 4.7 μm (column 6), 5.8 μm (column 7) and 9 μm (column 8).

DETAILED DESCRIPTION OF THE INVENTION

As noted above, the present invention is generally directed to compositions and methods for pulmonary gene delivery. It has been found, within the context of the present invention, that a gene complexed with a stabilizing agent (such as a cationic lipid carrier) may be efficiently formulated into an aerosol and delivered to a patient through the use of sonic nebulization. Accordingly, the present invention is particularly directed to compositions comprising a sonic nebulized nucleic acid/stabilizing agent complex, to sonic nebulizers containing such compositions, and to the use of such compositions for the delivery of therapeutic nucleic acid drugs to the respiratory tract of a patient.

It has also been found, within the context of the present invention, that the charge of a nucleic acid/stabilizing agent complex is an important factor influencing gene transfer efficiency via nebulization or intratracheal instillation. More specifically, positively charged complexes result in higher levels of transgene expression than negatively charged complexes, and the efficiency improves with an increase in the positive charge. Accordingly, the present invention is also directed to compositions comprising a nucleic acid/stabilizing agent complex having a charge ratio selected to enhance gene transfer (typically a ratio (−:+) of at least 1:2). Preferably, such complexes are nebulized prior to administration to a patient.

As used herein, the term "nebulized" refers to a complex that has been treated by jet or ultrasonic nebulization to form an aerosol, as described herein. The term "sonic nebulized" refers to a complex that has been treated by ultrasonic nebulization. Any commercially available nebulizer may be used to prepare nebulized complexes. For the preparation of sonic nebulized complexes, an ultrasonic nebulizer such as the Omron Model NE-U07 (Omron Health Care, Inc., Lake View, Ill.) may be employed. An ultrasonic nebulizer uses a piezoelectric transducer that vibrates at very high frequency to induce waves in the reservoir solution. Interference of these waves at the surface of the liquid leads to the production of droplets as an aerosol (i.e., a suspension of colloidal particles), which is then transported by an airstream. This method produces aerosols containing particles in the respirable range (typically 1–5 μm). Without wishing to be bound by any particular theory or mechanism of the present invention, it is believed that the high delivery efficiency of sonic nebulized nucleic acid/stabilizer complexes can be attributed to the fact that the sonic nebulizer operates in a passive mode and delivers aerosols as a bolus, only during inhalation, through a one way valve. This minimizes aerosol loss during exhalation.

While any nucleic acid molecule may be used in the preparation of nebulized nucleic acid/stabilizing agent complexes of the present invention, plasmid DNA and RNA molecules are preferred. Preferably, the size of the complex is less than 2 μm, to permit effective aerosol formation by the ultrasonic nebulizer. Preferred nucleic acid molecules are plasmid expression vectors containing genes of interest. Such plasmids may be prepared using techniques well known to those of ordinary skill in the art, such as the techniques found in Sambrook et al., *Molecular Cloning: A Laboratory Manual*, Cold Spring Harbor Laboratories, Cold Spring Harbor, N.Y., 1989. Preferred plasmids are those that encode a cytokine (such as, but not limited to, IL-12), the protease inhibitor alpha-1 antitrypsin, cystic fibrosis transmembrane regulator and other such proteins.

A "stabilizing agent" within the context of the present invention may be any compound or material that, when complexed to a nucleic acid molecule, permits ultrasonic nebulization of the complex without significant loss of transfection efficiency of the nucleic acid. Loss of the supercoiled form (the most potent and fragile of plasmid physical forms) upon nebulization should be less than 20%. Suitable stabilizing agents include one or more lipids, peptides and/or polymers. For example, a peptide/DNA complex containing a condensing peptide (GM208) and a lytic peptide (GM225.1) formulated at a charge ratio (−:+:−) of 1:3:1 is stable after nebulization, as indicated by particle size and zeta potential measurements. Lipids are preferred stabilizing agents, and cationic lipids, such as N-[1-(2,3-dioleyloxy)propyl]-N-N-N-trimethylammonium chloride (DOTMA), are particularly preferred. Cationic lipids are typically employed with helper lipids (or co-lipids) that facilitate the release of DNA from the endosomes following endocytic uptake of the nucleic acid/lipid complex by fusing with endosomal membranes and modulating their physical state. Suitable co-lipids include dioleylphosphatidylethanolamine (DOPE) and/or cholesterol (Chol) (see Brigham et al., *Am. J. Med. Sci.* 298:278–281, 1989; Canonica et al., *Am. J. Resp. Cell. Mol. Biol.* 10:24–29, 1994; Bennett et al., *Biosci. Rep.* 15:47–53, 1995). Lipids for use in the present invention may generally be obtained from commercial sources, such as Avanti Polar Lipids Inc. (Alabaster, Ala.).

In particularly preferred embodiments, the amounts and types of lipids are selected so as to generate a complex that results in enhanced gene transfer to respiratory epithelial cells following intratracheal instillation and/or aerosol inhalation. It has been found, within the context of the present invention, that particle size and charge are important factors that influence pulmonary transgene expression. These properties are determined by the cationic lipid, the co-lipid and methods of formulation. The size and charge ratio of nucleic acid/cationic lipid complexes can be varied by altering the stoichiometry of lipids and nucleic acid (see Tomlinson and Rolland, *J. Control. Rel.*, in press, 1996). The mean size of such complexes varies as a function of the relative level of cationic lipid (for instance, from 100 nm for a 1:0.5 (−:+) charge ratio to 220 nm for a 1:3 charge ratio). In addition, for a fixed DNA/lipid ratio, the increase in DNA concentration has been found to result in an increase in the mean diameter of the complex.

Complex size and surface charge may generally be evaluated using methods well known to those of ordinary skill in the art. For example, the charge ratio may be determined by Doppler electrophoretic light scattering. The mean diameter and zeta potential of the complexes may be characterized by dynamic light scattering and Doppler electrophoretic light scattering (see Tomlinson and Rolland, *J. of Cont. Rel.,* 39:357–372, 1996). Doppler electrophoretic light scattering may generally be performed using any suitable equipment, such as the Coulter DELSA 440 (Coulter Corp., Hialeah, Fla.). Such analyses may be performed by collecting the scattered light front four different angles. The frequency of operation of the instrument may be about 500 Hz with an amplitude of current equal to or lower than the conductivity of the sample. Any equipment suitable for performing dynamic light scattering analyses may be employed, including the Coulter N4 MD Sub-Micron Particle Size Analyzer (Coulter Corp., Hialeah, Fla.).

Figure 1:
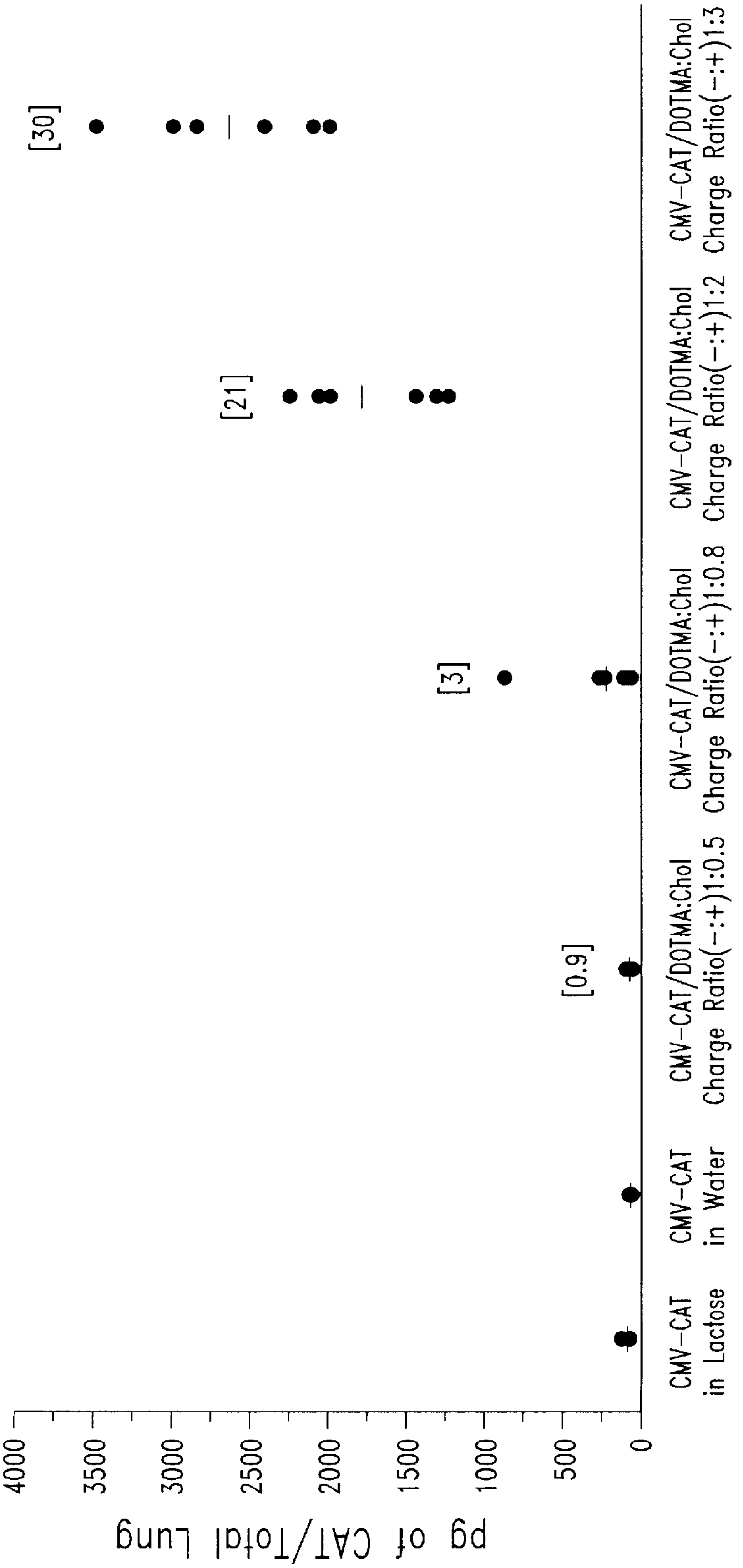
FIG. 1 is a graph that depicts the level of CAT expression (presented as pg CAT per total lung) in the rat lung following intratracheal instillation of representative nucleic acid/stabilizing agent complexes (containing 50 μg plasmid DNA) at different charge ratios. The charge ratios (−:+) evaluated were 1:0.5 (column 3), 1:0.8 (column 4), 1:2 (column 5) and 1:3 (column 6). The levels of expression observed following instillation of CMV-CAT in lactose (column 1) and in water (column 2) are also presented. For columns 3–6, the number in brackets represents the fold enhancement over naked DNA.

In general, positively charged complexes give higher levels of expression than negatively charged complexes (see FIG. 1). In addition, the level of transgene expression increases as the particle size of the complex increases (see FIGS. 2 and 3). Accordingly, nucleic acid/stabilizing agent complexes typically have a charge ratio (−:+) of at least 1:2, preferably ranging from 1:2 to 1:6, and more preferably about 1:3. Particle size of the nucleic acid/stabilizing agent complex should be greater than 200 nm for efficient uptake.

Nucleic acid and stabilizing agents may be formulated into a complex using any technique appropriate for the particular components. Such techniques are well known to those of ordinary skill in the art. In complexes containing one or more lipid stabilizing agents, large multilamellar vesicles (MLVs) or extruded liposomes (i.e., unilamellar vesicles) may be prepared prior to the addition of nucleic acid. For example, cationic liposomes composed of DOTMA, along with co-lipids DOPE or cholesterol at a 1:1 mole ratio, may be extruded through polycarbonate filters with different pore diameters (such as 200, 400 and 800 nm) to prepare unilamellar vesicles of different size. Small unilamellar vesicles (SUVs), which have diameters less than 100 nm, may also be prepared by extrusion through appropriately sized filters. Plasmid/lipid complexes may then be prepared by controlled mixing of the cationic liposomes with plasmid DNA at a pre-determined ratio (the stoichiometry of DNA to cationic lipids depends on charge and concentration) using a continuous infusion apparatus. Preferably, the complexes are prepared in 10% lactose so that the formulation is isotonic. Liposomes and plasmids may be delivered to the mixing chamber at a precise rate using, for example, a variable flow self-priming peristaltic pump (e.g., VWR Model Number 54856 (VWR, Houston, Tex.). Steady state conditions may be maintained in the mixing chamber such that the input flow rate of the components into the mixing chamber is equal to the output rate of the formulated complex from the mixing chamber. The complexation efficiency (ie., the fraction of plasmid condensed onto the cationic lipid) may be determined by agarose gel electrophoresis. Plasmid integrity may also be determined using agarose gel electrophoresis, by stripping the DNA from the complex with Triton X, and comparing the stripped DNA bands with that of a naked DNA control.

The colloidal stability of nucleic acid/stabilizing agent complexes is important for clinical applications. Studies have shown that formulated complexes aggregate over time (see Rolland et al., *Proc. Intern Symp. Contl. Rel. Bioact. Mat.* 21:240–241, 1994), resulting in decreased transfection efficiency. It has been found, within the context of the present invention, that the stability of complexes in an isotonic medium may be increased by lyophilizing the formulated complex in the presence of cryoprotectants (e.g., lactose, mannitol, sucrose and/or trehalose). For example, complexes formulated in lactose may be lyophilized at −30° C. using a freeze dryer (e.g., Model TDS2C0T500, FTS Systems Inc., Stone Ridge, N.Y.). The cooling down, primary cooling, secondary cooling and vacuum may be controlled using a microcomputer. Following freeze drying under controlled conditions and rehydration to isotonicity, the stability characteristics of the complex (size and zeta potential) are maintained (see FIG. 7).

The lyophilized complex may be jet milled to produce particles in the 1–3 μm range for preparation of a dry powder inhalation dosage form. Lyophilized and jet milled complexes that are rehydrated and instilled maintain their ability to transfect cells; moreover the transfection efficiency is comparable to plasmid/lipid complexes that are not lyophilized (see FIG. 6). Jet milling may be performed using, for example, Micro-Jet Model 00, Fluid Energy Aljet, Plumsteadville, Pa., with a 60 psig grinding pressure, a 50 psig feed pressure and a manual feed. Prior to administration to a patient, lyophilized and jet milled complexes should be rehydrated to isotonicity.

Nucleic acid/stabilizing agent complexes may be aerosolized using a ultrasonic nebulizer, such as the Omron Model NE-U07. This device produces aerosols by vibration of a piezoelectric crystal at high frequency (2.4 Hz). While other nebulizers may be employed, three parameters are of particular importance in nebulizer selection: the mass median aerodynamic diameter (MMAD), respirable dose (RD) and delivery efficiency, which may be determined using standard techniques. Preferably, the MMAD is less than about 5 μm, the RD is greater than about 60% and the delivery efficiency (ie., the ratio of the mass of drug deposited in the lower airways to the mass of drug aerosolized) is greater than about 10% (see Pillai et al., *J. Aerosol Med.* 9:227–240, 1996).

An aerosolized nucleic acid/stabilizing agent complex may be collected using, for example, a modified test tube impaction apparatus. Aerosols may be fed into a flexible tygon tubing and through a narrow glass pipet such that the aerosol particles that exit the pipet impact on an ice-cooled test tube and condense. In this manner, aerosols may be collected at predetermined time intervals.

Nucleic acid/stabilizing agent complexes prepared as described herein may generally be used for gene delivery to the respiratory tract of a patient. Within the context of the present invention, a patient may be a human or other mammal, and may be afflicted with one or more diseases or may be free of detectable disease. Accordingly, treatment of a patient with one or more nucleic acid/stabilizing agent complexes may be for preventive purposes or for treatment of an existing disease. For example, a complex containing nucleic acid encoding IL-12 could be administered by aerosol inhalation to modify the immune response to an allergen-induced asthma attack. The nucleic acid/stabilizing agent complexes described herein are suitable for administration by inhalation, which may be oral and/or nasal. Preferably, the complex is sonic nebulized, but jet nebulization may also be employed for complexes having a net positive charge, as described above.

For administration to a patient, one or more nucleic acid/stabilizing agent complexes are generally formulated as a pharmaceutical composition. A pharmaceutical composition comprises a nucleic acid/stabilizing agent complex in combination with a physiologically acceptable carrier (i.e., a non-toxic material that does not interfere with the activity of the active ingredient). Any suitable carrier known to those of ordinary skill in the art may be employed in the pharmaceutical compositions of the present invention. Representative carriers include synthetic particles carriers such as peptides and biodegradable polymers or a combination of such materials. Optionally, a pharmaceutical composition may additionally contain other additives such as, for example, preservatives, antimicrobial agents, anti-oxidants, chelating agents, inert gases, and/or other active ingredients.

The frequency of administration and dosage will vary from patient to patient, and depending on the particular nucleic acid administered, the bioavailability of the formulated plasmids to airway epithelial cells and the level and duration of gene expression. Because the protein encoded by the transgene is expressed at the target site, the dose required for prophylactic effect is orders of magnitude lower than that required for drug delivery by conventional routes, with concomitantly fewer side effects. In general, 1–2 doses may be administered every week, depending on the level of therapeutic protein required at the target site for prophylactic or therapeutic effect. A suitable dose is an amount of sonic nebulized/stabilzing agent complex that is sufficient to show improvement in the symptoms of a patient afflicted with a disease. Such improvement may be detected based on fewer systemic side effects, improved patient compliance and/or an improvement in clinical symptoms associated with the disease state. In general, the amount of sonic nebulized/stabilizing agent complex present in a dose ranges from about 500 μg to 4 mg. The emitted dose from the ultrasonic nebulizer for formulations detailed herein ranges from about 10 to 15 μg/L. The exposure time, estimated from the output concentration of aerosols, the ventilatory parameters for human beings under normal breathing conditions and, the deposition efficiency based on the mass median aerodynamic diameter (MMAD) of aerosols, may vary from about 15 minutes to about 2 hours.

The following Examples are offered by way of illustration and not by way of limitation.

EXAMPLES

Example 1

Preparation of Nucleic Acid/Stabilizing Agent Complex

This Example illustrates the preparation of a nucleic acid/stabilizing agent complex.

A plasmid containing the bacterial reporter gene chloramphenicol acetyl transferase (CAT) driven by the cytomegalovirus (CMV) promoter/enhancer was constructed using standard techniques. Unilamellar vesicles composed of the cationic lipid DOTMA with either DOPE or cholesterol (Chol) (all lipids obtained from Avanti Polar Lipids Inc., Alabaster, Ala.) at a 1:1 mole ratio were prepared by extrusion through filters (Poretics Corp., Livermore, Calif.) with pore diameters of 200, 400 and 800 nm.

Figure 2:
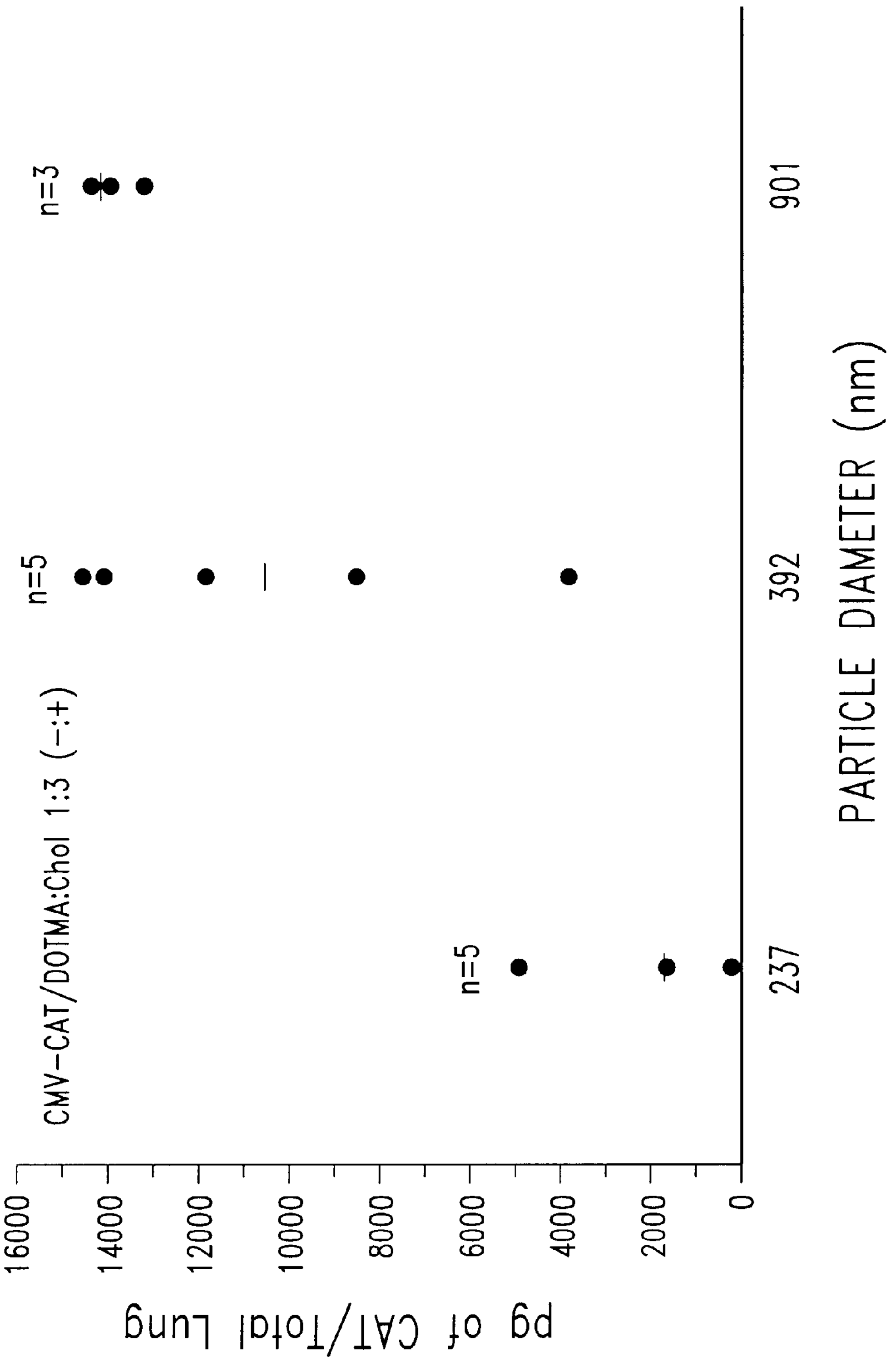
FIG. 2 is a graph depicting the level of CAT expression (presented as pg CAT per total lung) in the rat lung following intratracheal instillation of representative nucleic acid/stabilizing agent complexes (containing 50 μg plasmid DNA) formulated using liposomes of different sizes. The levels of expression of CMV-CAT/DOTMA:Chol having a charge ratio of 1:3 (−:+) are presented for complexes having particle diameters of 237 nm (column 1), 392 (column 2) and 901 (column 3).
Figure 3:
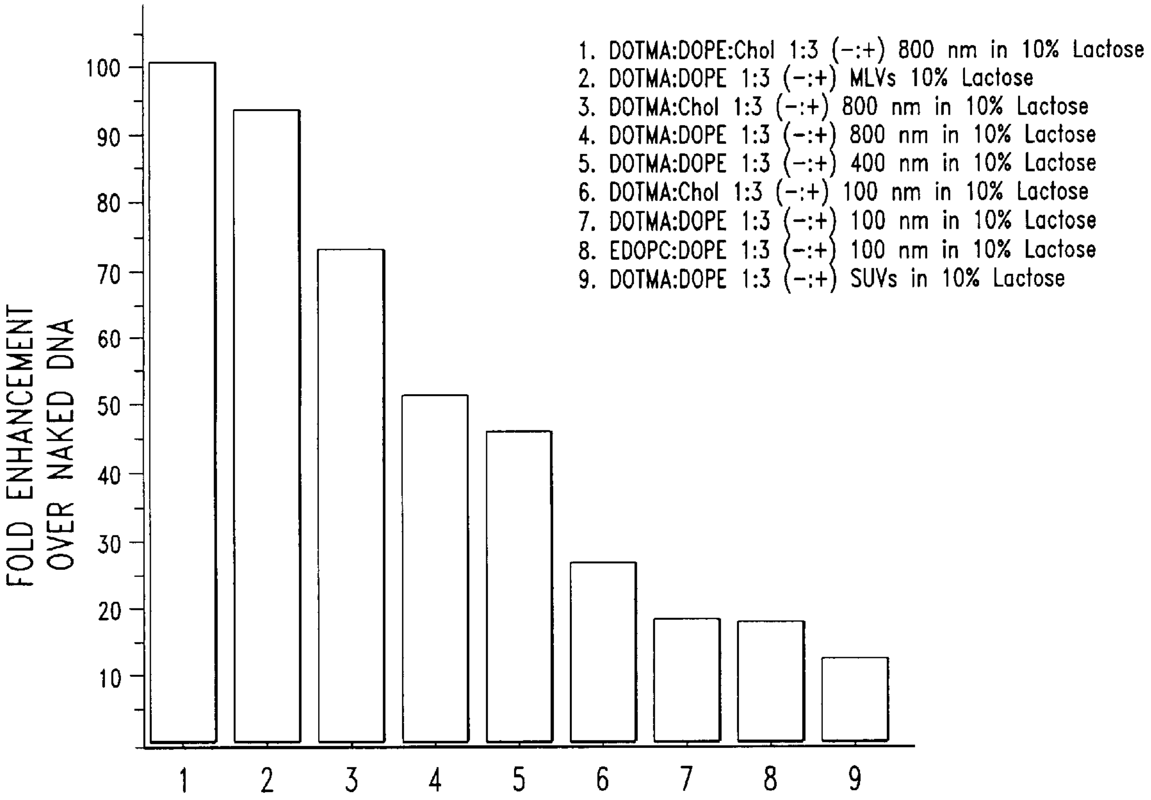
FIG. 3 is a histogram depicting the transfection efficiency for a series of representative nucleic acid/stabilizing agent complexes following intratracheal instillation. The level of expression is expressed as the fold enhancement over naked DNA. In each instance, the plasmid/lipid complexes were formulated at a charge ratio (−:+) of 1:3, using cationic liposomes extruded through polycarbonate filters with different pore diameters. The complexes were formulated in 10% lactose at a concentration of 125 μg/mL. The complexes evaluated (with filter pore size) were DOTMA-:DOPE:Chol 800 nm (column 1), DOTMA:DOPE MLVs (column 2), DOTMA:Chol 800 nm (column 3), DOTMA-:DOPE 800 nm (column 4), DOTMA:DOPE 400 nm (column 5), DOTMA:Chol 100 nm (column 6), DOTMA-:DOPE 100 nm (column 7), EDOPC (i.e., ethyldioleylphosphatidylcholine):DOPE 100 nm (column 7) and DOTMA:DOPE SUVs (column 8).

CMV-CAT/DOTMA:DOPE and CMV-CAT/DOTMA:Chol complexes at a charge ratio of 1:3 (−:+) were formulated in 10% (w/v) lactose by mixing the plasmid with the liposomes under controlled conditions using a continuous infusion apparatus. The plasmid DNA concentration was 200 μg/mL. The mean diameter and zeta potential of the complexes were characterized via dynamic light scattering, using a Coulter N4 MD Sub-Micron Particle Size Analyzer (Coulter Corp., Hialeah, Fla.), and via Doppler electrophoretic light scattering (Coulter DELSA 440 (Coulter Corp., Hialeah, Fla.)). Analyses were performed by collecting the scattered light from four different angles. The frequency of operation of the instrument was about 500 Hz and the amplitude of current was equal to or lower than the conductivity of the sample. The mean diameters were as shown in FIG. 2, and the zeta potential measurements showed that overall charge on the complexes was positive. The complexation efficiency was determined by agarose gel electrophoresis and found to be 100% for complexes prepared at a charge ratio (−:+) of 1:3.

Example 2

Preparation of an Aerosol Sonic Nebulized Nucleic Acid/Stabilizing Agent Complex This Example illustrates the generation and characterization of an aerosol complex.

The plasmid/lipid complexes described in Example 1 were aerosolized according to the manufacturer's instructions using an ultrasonic nebulizer (Model NE-U07, Omron Health Care, Inc., Lake View, Ill.). Aerosolized complexes were collected using a modified test tube impaction apparatus. In this system, the aerosols were fed into a flexible tygon tubing and through a narrow glass pipet. The aerosols that exited the pipet impacted on the ice-cooled test tube and condensed. Aerosols were collected at predetermined time intervals for characterization, as described below.

Stability of the sonic nebulized plasmid/lipid complexes and the DNA within the complexes were assessed using dynamic light scattering and Doppler electrophoretic light scattering as described above. The complexation efficiency and plasmid integrity were determined by agarose gel electrophoresis. For plasmid integrity determinations, the DNA was stripped from the complex by treatment with Triton-X prior to electrophoresis. The structure of the DNA bands in the Triton-treated samples was compared to that of a naked DNA control.

FIG. 8 shows that the fraction of supercoiled plasmid in the unnebulized and nebulized complexes was similar to that in the "naked DNA" control. Supercoiled form is the most potent and fragile of plasmid physical forms. The fact that the integrity of the supercoiled form was maintained after nebulization indicates that cationic lipids aid in protecting the DNA from shear induced during droplet formation.

The emitted dose and aerodynamic diameter were determined using standard methods as defined in United States Pharmacopeia <601>. Aerosols were collected on a 0.2 μm filter at a pre-determined flow rate of 3 L/min using a critical flow orifice (CFO). The filter containing the aerosols was washed with 5 mL of 5% sodium dodecyl sulfate (SDS) buffer to separate the DNA from the lipids. The solution was centrifuged and assayed spectrophotometrically at a wavelength of 260 nm for DNA concentration. The DNA concentration in the output aerosol stream from the ultrasonic nebulizer was 5 μg/mL.

Aerosols generated from the ultrasonic nebulizer were characterized based on mass median aerodynamic diameter (MMAD) and geometric standard deviation (GSD) using inertial impaction techniques. An Andersen 1 SCFM (28.3 L/min) non-viable ambient sampler, consisting of eight impaction stages and a preseparator, was employed to collect aerosol particles. The aerosols were collected for 5 minutes. Aerosols were collected at each of the eight impaction stages on stainless steel discs and on a glass fiber filter (Gelman Type A/E, Gelman Sciences Inc., Ann Arbor, Mich.) with pore diameter of 0.2 μm. Each of the discs was removed from the impactor, placed in a petri dish and washed with 5 mL of 5% SDS. Each petri dish was shaken at periodic intervals for complete dissolution of the lipid from the deposited particles. The solution was centrifuged and assayed spectrophotometrically at a wavelength of 260 nm for DNA concentration. The cumulative mass fraction of DNA collected on each stage of the cascade impactor was plotted against the effective cut-off diameter for that stage on logarithmic probability paper and a log-normal distribution was calculated for the data by the method of least squares. The MMAD (taken as the point on the regression which equally divided the mass) was 2.4 μm. The GSD (calculated by dividing the particle size below which 84.1% of the distribution by mass occurs by the mass median size) was 3.2. The size distribution of the aerosols (shown in FIG. 9) indicates that the majority of the particles are in the respirable range.

Example 3

Lung Instillation of Plasmid/Lipid Complex

This Example illustrates the level of transgene expression following intratracheal instillation of unnebulized and nebulized plasmid/lipid complexes.

Animals were divided into three treatment groups (three animals/group) and anesthetized with 80 mg/kg of ketamine given intraperitonealy. The treatment groups were intubated with a tracheal catheter and place supine above an operating table. Aerosols were delivered through the tracheal catheter and carried by the ventilating air stream. Animals were exposed to the aerosolized complex for pre-determined time intervals. Following inhalation, the animals were extubated and allowed to recover from the anesthetic and returned to the animal housing facility. The animals were euthanized by $CO_2$ asphyxiation 48 hours post-inhalation using a dry ice chamber and the lung tissues were harvested. The tissues were homogenized in Tris/HCl buffer and centrifuged. The supernatant was subsequently analyzed using the ELISA assay for CAT expression according to the manufacturer's instructions (Boehringer Mannheim CAT ELISA Kit, Catalog Number 1363727).

Figure 4:
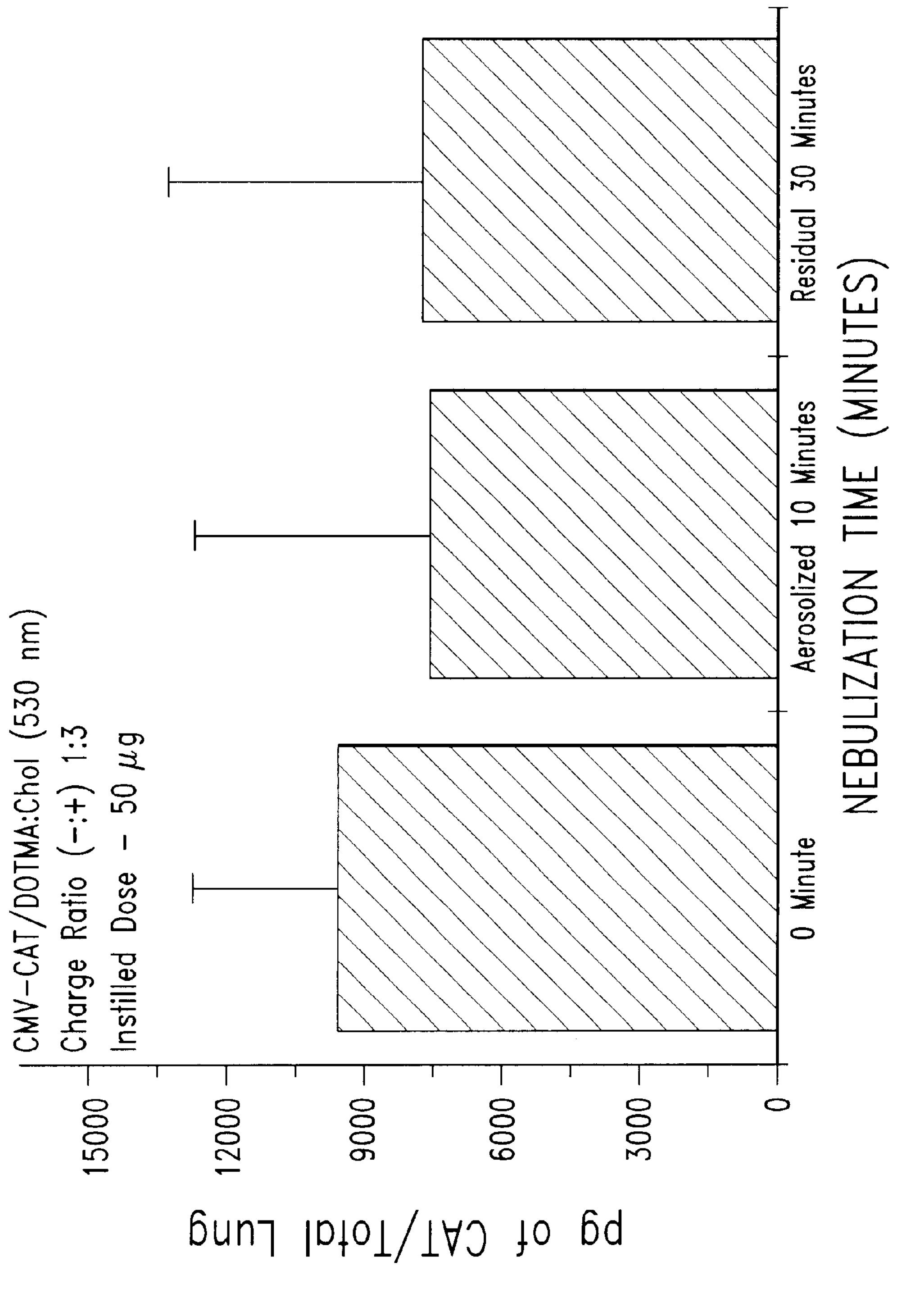
FIG. 4 is a histogram that shows the level of CAT expression in the rat lung (presented as pg of CAT per total lung) following intratracheal instillation of 50 μg of a representative unnebulized nucleic/acid stabilizing agent complex (column 1), or a nebulized (column 2) or residual (column 3) complex from the ultrasonic nebulizer. In each instance, the complex was CMV-CAT/DOTMA:Chol (530 nm diameter, 1:3 (−:+) charge ratio). Columns 2 and 3 show the level of expression for the complex following nebulization for 10 and 30 minutes, respectively.

FIG. 4, discussed further below, shows the levels of CAT expression in animals instilled by intratracheal intubation with 400 μl of the sonic nebulized complex (after 10 minutes, collected on an inpinger) or residual complex aliquoted after 30 minutes from the nebulizer reservoir (100 μg of plasmid DNA). The results show that the level of transgene expression following intratracheal instillation of unnebulized, nebulized or residual plasmid/lipid complexes was comparable.

Example 4

The Effect of Charge on Transfection Efficiency

This Example illustrates the effect of complex charge on in vivo transfection efficiency of nucleic acid/stabilizing agent complexes comprising the cationic lipid DOTMA with co-lipids DOPE and cholesterol.

Cationic lipids and co-lipids were formulated as large multilamellar vesicles (MLVs) or unilamellar vesicles prepared by extrusion through polycarbonate membrane filters with varying pore diameters (100, 400 or 800 nm). CMV-CAT/DOTMA:Chol complexes at varying charge ratios were formulated in 10% (w/v) lactose as described in Example 1.

The level of CAT expression in rat lungs following intratracheal instillation of plasmid/lipid complexes (125 μg/mL plasmid DNA) was evaluated by ELISA assay, as discussed above. The results (shown in FIG. 1) show that increasing the charge ratio over the range of ratios evaluated results in an increased level of CAT expression.

Example 5

The Effect of Particle Size on Transfection Efficiency

This Example illustrates the effect of particle size on in vivo transfection efficiency of nucleic acid/stabilizing agent complexes comprising the cationic lipid DOTMA with colipids DOPE and cholesterol.

Cationic lipids and co-lipids were formulated as large multilamellar vesicles (MLVs) or extruded through polycarbonate membrane filters with varying pore diameters (100, 400 and 800 nm). CMV-CAT/DOTMA:Chol and CMV-CAT/DOTMA:DOPE complexes with varying particle diameters and a fixed charge ratio of 1:3 (−:+) were formulated in 10% (w/v) lactose as described in Example 1. The plasmid DNA concentration was 125 μg/mL. The mean diameter and zeta potential of the complexes were characterized by dynamic light scattering and Doppler electrophoretic light scattering and the complexation efficiency was determined by agarose gel electrophoresis, as described above.

The data shown in FIG. 2 demonstrate that the level of transgene expression increases as the particle size of the complex increases from 237 to 901 nm. In addition (FIG. 3), the level of expression observed after intratracheal instillation with the formulation having a charge ratio of 1:3 was more than 100 fold higher than with unformulated DNA (uncondensed DNA in water or lactose).

Example 6

The Effect of Nebulization on Transfection Efficiency

This Example illustrates the transfection efficiency of nebulized nucleic acid/stabilizing agent complexes.

CMV-CAT/DOTMA:Chol complexes (530 nm diameter, 1:3 (−:+) charge ratio) were prepared as described above. The optimized plasmid/lipid complexes with controlled colloidal and surface properties, which gave high levels of transgene expression following intratracheal instillation, were then aerosolized using an ultrasonic nebulizer. These complexes were aerosolized using an ultrasonic nebulizer to assess the stability of the plasmids and the plasmid/lipid complexes, as well as in vivo transgene expression in rat lungs following intratracheal instillation and inhalation of the aerosolized complex. The DNA remained complexed to the cationic liposomes and the integrity of the plasmid was maintained (see FIG. 8, showing that the fraction of supercoiled form of plasmid in pre- and post-nebulized samples was similar). The mean diameter of the complex before nebulization was 530±329 nm. The mean diameter of the complex remaining in the nebulizer after nebulization for 10 or 20 minutes was 481±289 and 510±361 nm, respectively. Zeta potential measurements showed that the surface charge of the particles was unchanged after the nebulization process. These findings demonstrate that the colloidal properties of the plasmid/lipid complex were maintained after nebulization and that the binding of DNA to cationic liposomes can protect the DNA from shear induced during droplet formation.. The mass median aerodynamic diameter (MMAD) of aerosols generated using the ultrasonic nebulizers was less than 5 μm, indicating that the particles are in the respirable range (see FIG. 9).

The level of CAT expression in rat lungs following intratracheal instillation (without nebulization and with ultrasonic nebulization for 10 or 30 minutes) was then assessed as described above. The animals were anesthetized with 80 mg/kg of ketamine given intraperitonealy and were divided into three treatment groups (3 animals/group). The treatment groups were instilled by intratracheal intubation with 400 μl (100 μg plasmid DNA) of the nebulized or residual complex aliquoted from the reservoir. Animals instilled with the unnebulized complex served as the positive control. The animals were euthanized by $CO_2$ asphyxiation 48 hours post-instillation, using a dry ice chamber and the lung tissues were harvested. The tissues were homogenized in Tris-HCl buffer and centrifuged. The supernatant was subsequently analyzed using the ELISA assay for CAT expression.

The results, presented in FIG. 4, show that the expression levels obtained with the nebulized and residual complex were comparable. These findings indicate that the transfection efficiency of the plasmid DNA was maintained after nebulization.

We also assessed the in vivo transfection efficiency of lyophilized and jet milled plasmid/lipid complex delivered to the rat lungs by intratracheal instillation as rehydrated suspensions. We have developed methods for lyophilizing the formulated material in the presence of cryoprotectants to increase the stability of plasmid/lipid complexes in isotonic media. Complexes formulated in lactose were lyophilized at −30° C. under controlled conditions with specific cryoprotectants (lactose and mannitol) using a freeze dryer (Model TDS2C0T500, FTS Systems Inc., Stone Ridge, N.Y.). The cooling down, primary cooling, secondary cooling and vacuum were controlled using a microcomputer. Jet milling was performed using for Micro-Jet Model 00, Fluid Energy Aljet, Plumsteadville, Pa., with a 60 psig grinding pressure, a 50 psig feed pressure and a manual feed. Lyophilized and jet-milled complexes were then rehydrated to isotonicity.

FIG. 6 presents the results of an experiment that assessed the level of CAT expression in the rat lung following intratracheal instillation of lyophilized and jet-milled DNA/lipid complex. The lyophilized and jet milled complexes that were rehydrated and instilled maintained their ability to transfect lung cells. In addition, the transfection efficiency was comparable to that of the plasmid/lipid complex that was not lyophilized.

As shown in FIG. 7, the stability characteristics (size and zeta potential) of freeze-dried and rehydrated CMV-CAT/DOTMA:Chol complexes (with a 1:2 (−:+) charge ratio) remain unchanged over a period of at least four months. Transfection efficiency was also found to be stable over this time period.

Example 7

Transgene Expression Following Inhalation of Nucleic Acid/Stabilizing Agent Complexes This Example illustrates the level of transgene expression in the lung following nasal or oral inhalation of a nucleic acid/stabilizing agent complex.

CMV-CAT/DOTMA:Chol complexes (813 nm diameter, 1:3 (−:+) charge ratio) were prepared as described above. These complexes were aerosolized using a jet and ultrasonic nebulizer and were administered to rats using a nose only exposure chamber or via a tracheal catheter, as described above. For nasal exposure, the nose-only exposure chamber consisted of an aerosol inlet section with horizontal side branches and an aerosol exhaust section. The inlet section was maintained at a higher pressure compared to the exhaust. The aerosolized complex entered the chamber through the top, flowed around the animal's nose and exited through a series of holes around the nose of the animal. The chamber was operated such that the aerosol concentration was uniform at the top and bottom port. Animals were exposed to the aerosolized complex for pre-determined time intervals. Following exposure, the animals were removed from the tube, placed in their respective cages and returned to the animal housing facility. Forty eight hours following exposure the lung tissues were harvested and assayed as described above.

Figure 5:
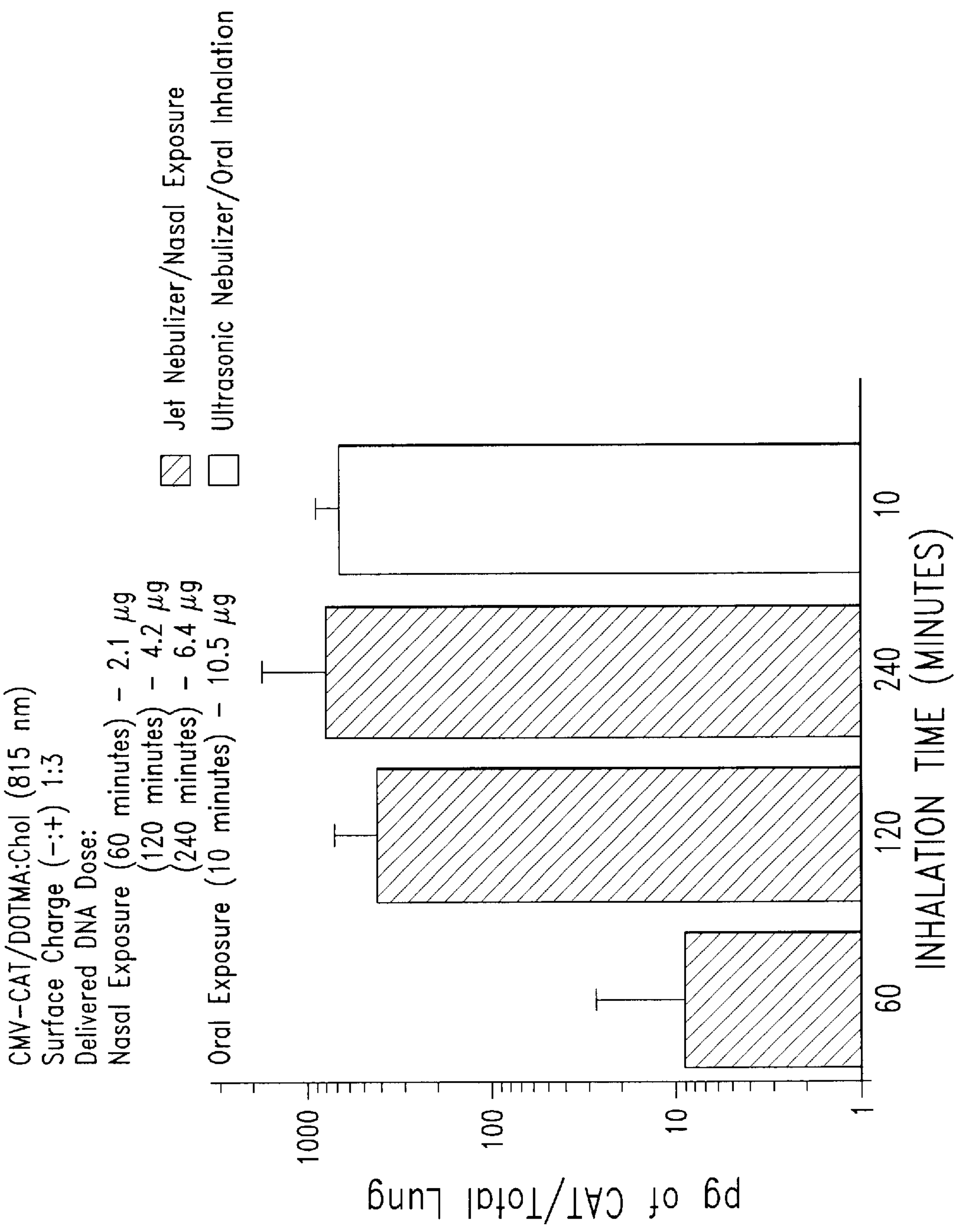
FIG. 5 is a histogram depicting the level of CAT expression (in pg CAT per total lung) following inhalation of representative aerosolized nucleic acid/stabilizing agent complexes following nebulization with a jet or ultrasonic nebulizer. In each instance, the complex was CMV-CAT:DOTMA:Chol (815 nm diameter and 1:3 (−:+charge). Columns 1–3 show the level of expression following jet nebulization and nasal exposure. For column 1, the inhalation time was 60 minutes and the delivered DNA dose was 2.1 μg (estimated); in column 2, the inhalation time was 120 minutes and the delivered DNA dose was 4.2 μg (estimated) and in column 3 the inhalation time was 240 minutes and the delivered DNA dose was 6.4 μg (estimated). Column 4 shows the level of expression following ultrasonic nebulization and oral inhalation for 10 minutes, with a delivered DNA dose of 10.5 μg (estimated). In each case, the dose of aerosol deposited in the animals' lungs was estimated using the following formula.

The levels of CAT expression in the lung, shown in FIG. 5, demonstrate that oral inhalation and nasal exposure of aerosolized complexes produces transgene expression. Further, ultrasonic nebulized complexes can achieve levels of DNA delivery and transgene expression comparable to those achieved by jet nebulized complexes, but at significantly lower inhalation times.

From the foregoing, it will be appreciated that, although specific embodiments of the invention have been described herein for the purpose of illustration, various modifications may be made without deviating from the spirit and scope of the invention.

What is claimed is:

1. A method for preparing a sonic nebulized nucleic acid/stabilizing agent complex, comprising the steps of:

(a) admixing a nucleic acid and a stabilizing agent comprising cationic liposomes at a negative to positive charge ratio ranging from about 1:2 to about 1:6 to form a positively charged nucleic acid/stabilizing agent complex;

(b) formulating the positively charged nucleic acid/stabilizing agent complex in a physiologically acceptable carrier to form a stabilized nucleic acid formulation; and (c) aerosolizing said formulation with a sonic nebulizer.

2. The method of claim 1 wherein the cationic liposomes comprise a cationic lipid and a neutral co-lipid.

3. The method of claim 1 wherein the cationic liposomes comprise lipids selected from the group consisting of: DOTMA; DOTMA:Cholesterol; DOTMA:DOPE; and DOTMA:DOPE:Cholesterol.

4. The method of claim 1 wherein the formulation further comprises a cryoprotectant, and is lyophilized and rehydrated prior to aerosolizing.

5. The method of claim 4 wherein the cryoprotectant comprises a sugar selected from the group consisting of: lactose, mannitol, sucrose, and trehalose.

6. The method of claim 5 wherein the cryoprotectant comprises 10% lactose.

7. The method of claim 1 wherein the cationic liposomes have a diameter equal to or greater than about 100 nm prior to complexing with the nucleic acid.

8. The method of claim 1 wherein the cationic liposomes have a diameter equal to or greater than about 200 nm prior to complexing with the nucleic acid.

9. The method of claim 1 wherein the cationic liposomes have a diameter equal to or greater than about 400 nm prior to complexing with the nucleic acid.

10. The method of claim 1 wherein the cationic liposomes have a diameter equal to or greater than about 800 nm prior to complexing with the nucleic acid.

11. The method of claim 1 wherein the nucleic acid is a DNA sequence.

12. The method of claim 11 wherein the DNA sequence encodes a cytokine.

13. The method of claim 11 wherein the DNA sequence encodes alpha-1 antitrypsin or cystic fibrosis transmembrane regulator.

14. A nucleic acid delivery apparatus comprising a sonic nebulizer in fluid communication with a stabilized nucleic acid formulation comprising a nucleic acid/stabilizing agent complex wherein the complex is prepared by admixing nucleic acid molecules with cationic liposomes at a charge ratio ranging from about 1:2 to about 1:6 (−/+).

15. The nucleic acid delivery appartus of claim 14 wherein the cationic liposomes have a diameter equal to or greater than about 100 nm prior to admixing with nucleic acid.

16. The nucleic acid delivery apparatus of claim 14 wherein the cationic liposomes have a diameter equal to or greater than about 200 nm prior to admixing with the nucleic acid.

17. The nucleic acid delivery apparatus of claim 14 wherein the cationic liposomes have a diameter equal to or greater than about 400 nm prior to admixing with the nucleic acid.

18. The nucleic acid delivery apparatus of claim 14 wherein the cationic liposomes have a diameter equal to or greater than about 800 nm prior to admixing with the nucleic acid.

19. The nucleic acid delivery apparatus of claim 14 wherein the cationic liposomes further comprise a neutral co-lipid.

20. The nucleic acid delivery apparatus of claim 14 wherein the cationic liposomes comprise lipids selected from the group consisting of: DOTMA; DOTMA:Cholesterol; DOTMA:DOPE; and DOTMA:DOPE:Cholesterol.

21. The nucleic acid delivery apparatus of claim 14 wherein the nucleic acid/stabilizing agent complex is prepared by admixing nucleic acid molecules with cationic liposomes at a charge ratio of about 1:3 (−/+).

22. A method for improving the transfection efficiency of aerosolized DNA comprising:

(a) preparing a stabilized DNA formulation comprising a positively charged DNA/cationic lipid complex formed by admixing a solution of DNA with a suspension of cationic liposomes at a charge ratio ranging from about 1:2 to about 1:6 (−/+);

(b) aerosolizing the stabilized DNA formulation using an ultrasonic nebulizer; and (c) introducing the aerosolized stabilized DNA formulation into an airway of a mammal.

* * * * *